US00PP23656P2

(12) United States Plant Patent
Bergman

(10) Patent No.: US PP23,656 P2
(45) Date of Patent: Jun. 11, 2013

(54) ***HIBISCUS* PLANT NAMED 'ANTIGUA WIND'**

(50) Latin Name: *Hibiscus rosa-sinensis*
Varietal Denomination: Antigua Wind

(75) Inventor: Wendy R. Bergman, Hollister, CA (US)

(73) Assignee: Aris Horticulture, Inc., Barberton, OH (US)

( * ) Notice: Subject to any disclaimer, the term of this patent is extended or adjusted under 35 U.S.C. 154(b) by 0 days.

(21) Appl. No.: 13/373,928

(22) Filed: Dec. 5, 2011

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Annette Para
(74) *Attorney, Agent, or Firm* — C. A. Whealy

(57) ABSTRACT

A new and distinct cultivar of *Hibiscus* plant named 'Antigua Wind', characterized by its upright, somewhat outwardly spreading, uniformly mounded and dense plant habit appropriate for container production; glossy dark green-colored leaves; uniform, freely and early flowering habit; large dark red-colored flowers; and good postproduction and garden performance.

2 Drawing Sheets

Botanical designation: *Hibiscus rosa-sinensis*.
Cultivar denomination: 'ANTIGUA WIND'.

BACKGROUND OF THE INVENTION

The present invention relates to a new and distinct *Hibiscus* plant, botanically known as *Hibiscus rosa-sinensis* and hereinafter referred to by the name 'Antigua Wind'.

The new *Hibiscus* plant is a product of a planned breeding program conducted by the Inventor in Alva, Fla. The objective of the breeding program is to create new freely-branching *Hibiscus* plants with a dense, uniform and compact plant habit appropriate for container production, early and uniform flowering habit, numerous flowers per lateral branch, desirable flower color and good garden performance.

The new *Hibiscus* plant originated from a cross-pollination made by the Inventor in Alva, Fla. in September, 2007 of a proprietary selection of *Hibiscus rosa-sinensis* identified as code number YB-2450, not patented, as the female, or seed, parent with a proprietary selection of *Hibiscus rosa-sinensis* identified as code number YB-2541, not patented, as the male, or pollen, parent. The new *Hibiscus* plant was discovered and selected by the Inventor as a single flowering plant within the progeny of the stated cross-pollination in a controlled greenhouse environment in Alva, Fla. on Sep. 5, 2008.

Asexual reproduction of the new *Hibiscus* plant by vegetative terminal cuttings in a controlled greenhouse environment in Alva, Fla. since February, 2009 has shown that the unique features of this new *Hibiscus* plant are stable and reproduced true to type in successive generations.

SUMMARY OF THE INVENTION

Plants of the new *Hibiscus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Antigua Wind'. These characteristics in combination distinguish 'Antigua Wind' as a new and distinct *Hibiscus* plant:

1. Upright, somewhat outwardly spreading, uniformly mounded and dense plant habit appropriate for container production.
2. Glossy dark green-colored leaves.
3. Uniform, freely and early flowering habit.
4. Large dark red-colored flowers.
5. Good postproduction and garden performance.

Plants of the new *Hibiscus* can be compared to plants of the female parent selection. Plants of the new *Hibiscus* differ from plants of the female parent selection in the following characteristics:

1. Plants of the new *Hibiscus* are more outwardly spreading than plants of the female parent selection.
2. Plants of the new *Hibiscus* have smaller flowers than plants of the female parent selection.
3. Plants of the new *Hibiscus* and the female parent selection differ in flower color as plants of the female parent selection have lighter red-colored flowers.

Plants of the new *Hibiscus* can be compared to plants of the male parent selection. Plants of the new *Hibiscus* differ from plants of the male parent selection primarily in flower color as plants of the male parent selection have dark pink-colored flowers with burgundy-colored centers.

Plants of the new *Hibiscus* can be compared to plants of the *Hibiscus rosa-sinensis* 'Brilliant Red', not patented. In side-by-side comparisons conducted in Alva, Fla., plants of the new *Hibiscus* differed from plants of 'Brilliant Red' in the following characteristics:

1. Plants of the new *Hibiscus* were more upright than plants of 'Brilliant Red'.
2. Plants of the new *Hibiscus* were more freely branching than plants of 'Brilliant Red'.
3. Plants of the new *Hibiscus* had smaller flowers than plants of 'Brilliant Red'.
4. Plants of the new *Hibiscus* and 'Brilliant Red' differed in flower color as plants of 'Brilliant Red' had lighter red-colored flowers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Antigua Wind' grown in a container.

The photograph on the second sheet comprises a close-up view of a typical flowering plant of 'Antigua Wind'.

DETAILED BOTANICAL DESCRIPTION

The aforementioned photographs and following observations, measurements and values describe plants grown during the summer in 15-cm containers in a fiberglass-covered greenhouse in Alva, Fla. and under environmental conditions and cultural practices which closely approximate commercial *Hibiscus* production. During the production of the plants, day temperatures ranged from 20° C. to 38° C., night temperatures ranged from 15° C. to 24° C. and light levels ranged from 3,000 to 4,000 foot-candles. Plants were pinched two times and were 27 weeks old when the photographs and the description were taken. In the description, color references are made to The Royal Horticultural Society Colour Chart, 2007 Edition, except where general terms of ordinary dictionary significance are used.

Botanical classification: *Hibiscus rosa-sinensis* 'Antigua Wind'.

Parentage:

*Female, or seed, parent*.—Proprietary selection of *Hibiscus rosa-sinensis* identified as code number YB-2450, not patented.

*Male or pollen parent*.—Proprietary selection of *Hibiscus rosa-sinensis* identified as code number YB-2541, not patented.

Propagation:

*Type*.—By vegetative terminal cuttings.

*Time to initiate roots*.—About 10 days at temperatures of 24° C.

*Time to develop roots*.—About four weeks at temperatures of 24° C.

*Root description*.—Thick, fibrous; white in color.

*Rooting habit*.—Moderate branching; moderately dense.

Plant description:

*Plant form and growth habit*.—Perennial, evergreen, upright, somewhat outwardly spreading, compact, uniformly mounded and dense; moderately vigorous to vigorous growth habit.

*Branching habit*.—Freely branching habit with lateral branches potentially develop at every node; pinching enhances lateral branch development.

*Plant height*.—About 34 cm.

*Plant diameter* (*area of spread*).—About 45 cm.

Lateral branch description:

*Length*.—About 24.5 cm.

*Diameter*.—About 7.5 mm.

*Internode length*.—About 2.75 cm.

*Aspect*.—Upright to outwardly spreading.

*Texture*.—Immature, smooth; mature, woody and rough.

*Color, immature*.—Close to 146A.

*Color, mature*.—Close to 197A to 197B.

Foliage description:

*Arrangement*.—Alternate, single; numerous; symmetrical.

*Length*.—About 9.5 cm.

*Width*.—About 8.5 cm.

*Shape*.—Cordate.

*Apex*.—Acute.

*Base*.—Cordate.

*Margin*.—Crenate.

*Texture, upper and lower surfaces*.—Smooth, glabrous.

*Luster, upper surface*.—Glossy.

*Luster, lower surface*.—Somewhat glossy.

*Venation pattern*.—Pinnate; arcuate.

*Color*.—Developing leaves, upper surface: More green than N137A. Developing leaves, lower surface: Close to 137B. Fully expanded leaves, upper surface: Much darker green than 147A; venation, darker green than 147A. Fully expanded leaves, lower surface: Close to N137B; venation, more green than 146A.

*Petiole*.—Length: About 4.4 cm. Diameter: About 4 mm. Texture, upper and lower surfaces: Slightly pubescent. Color, upper and lower surfaces: Close to 147A.

Flower description:

*Flower arrangement and flowering habit*.—Rounded star-shaped flowers arranged at terminal leaf axils; uniform and freely flowering habit with about three flowers per terminal; flowers face mostly upright.

*Natural flowering season*.—Plants of the new *Hibiscus* flower naturally during the spring and summer or during periods of warm weather; plants flower year-round in the greenhouse.

*Flower longevity*.—Flowers last about two to three days on the plant; flowers persistent.

*Flower diameter*.—About 13 cm.

*Flower length* (*height*).—About 8.5 cm.

*Flower bud*.—Resistance to abscission during shipping: Plants of the new *Hibiscus* have been observed to resist flower bud drop when stored in a closed box for five days at 13° C. Length: About 2.25 cm. Diameter: About 1.2 cm. Shape: Ovoid. Color: Darker green than 144A.

*Petals*.—Arrangement: Corolla consists of five petals that are fused at base; petals imbricate. Length: About 8.5 cm. Width: About 7.2 cm. Shape: Roughly spatulate. Apex: Rounded. Base: Attenuate. Margin: Entire; slightly undulate. Texture: Smooth, glabrous; velvety; veins prominent on the lower surface. Color: When opening, upper surface: Close to 45A to 45B. When opening, lower surface: Close to 47A. Fully opened, upper surface: Close to 45A to 45B; color does not fade with development. Fully opened, lower surface: Close to 47A; color does not fade with development.

*Sepals*.—Appearance: Five sepals fused into a tubular star-shaped calyx. Length: About 3.2 cm. Width: About 1.2 cm. Shape: Lanceolate. Apex: Sharply acute. Margin: Entire. Texture, upper surface: Smooth, glabrous; waxy. Texture, lower surface: Slightly pubescent. Color, upper and lower surfaces: Close to 144A.

*Bracts*.—Appearance: About seven fused at base. Length: About 1.5 cm. Width: About 5 mm. Shape: Lanceolate. Apex: Acute. Margin: Entire. Texture, upper surface: Smooth, glabrous. Texture, lower surface: Sparsely pubescent. Color, upper and lower surfaces: More green than 147A.

*Peduncles*.—Length: About 2.75 cm. Diameter: About 2.25 mm. Aspect: Upright to slightly outward. Strength: Strong, flexible. Texture: Smooth, glabrous. Color: More green than 146A.

*Reproductive organs*.—Androecium: Stamen number: Numerous, about 40 per flower. Filament length: About 5 mm. Filament color: Close to 46A. Anther shape: Oblong. Anther length: About 1 mm. Anther color: Close to 9A. Amount of pollen: Scarce. Pollen color: Close to 12A. Gynoecium: Pistil number: One per flower. Pistil length: About 8.7 cm. Style length: About 7 cm. Style texture: Smooth, glabrous; waxy. Style color: Close to 46A. Stigma appearance: Five-parted, rounded. Stigma color: Close to 46A. Ovary color: Close to 11D.

*Seeds and fruits*.—Seed and fruit production has not been observed on plants of the new *Hibiscus*.

Garden performance: Plants of the new *Hibiscus* have been observed to have good garden performance and to tolerate wind, rain and temperatures ranging from about 1° C. to about 38° C.

Pathogen & pest resistance: Plants of the new *Hibiscus* grown under Florida production conditions have not been shown to be susceptible to pathogens common to Hibiscus such as *Pseudomonas, Pythium* and *Phytophthora*. Plants of the new *Hibiscus* have not been observed to be resistant to pests and other pathogens.

It is claimed:

1. A new and distinct *Hibiscus* plant named 'Antigua Wind' as illustrated and described.

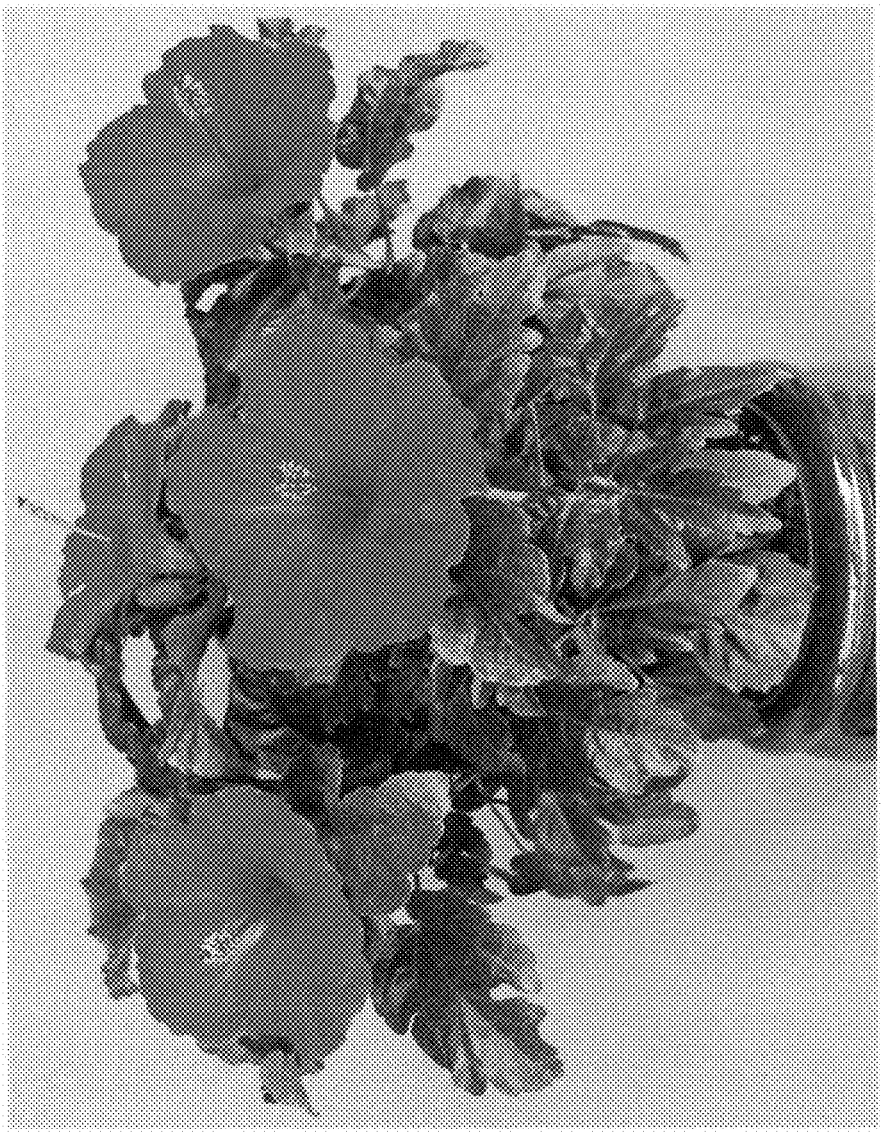

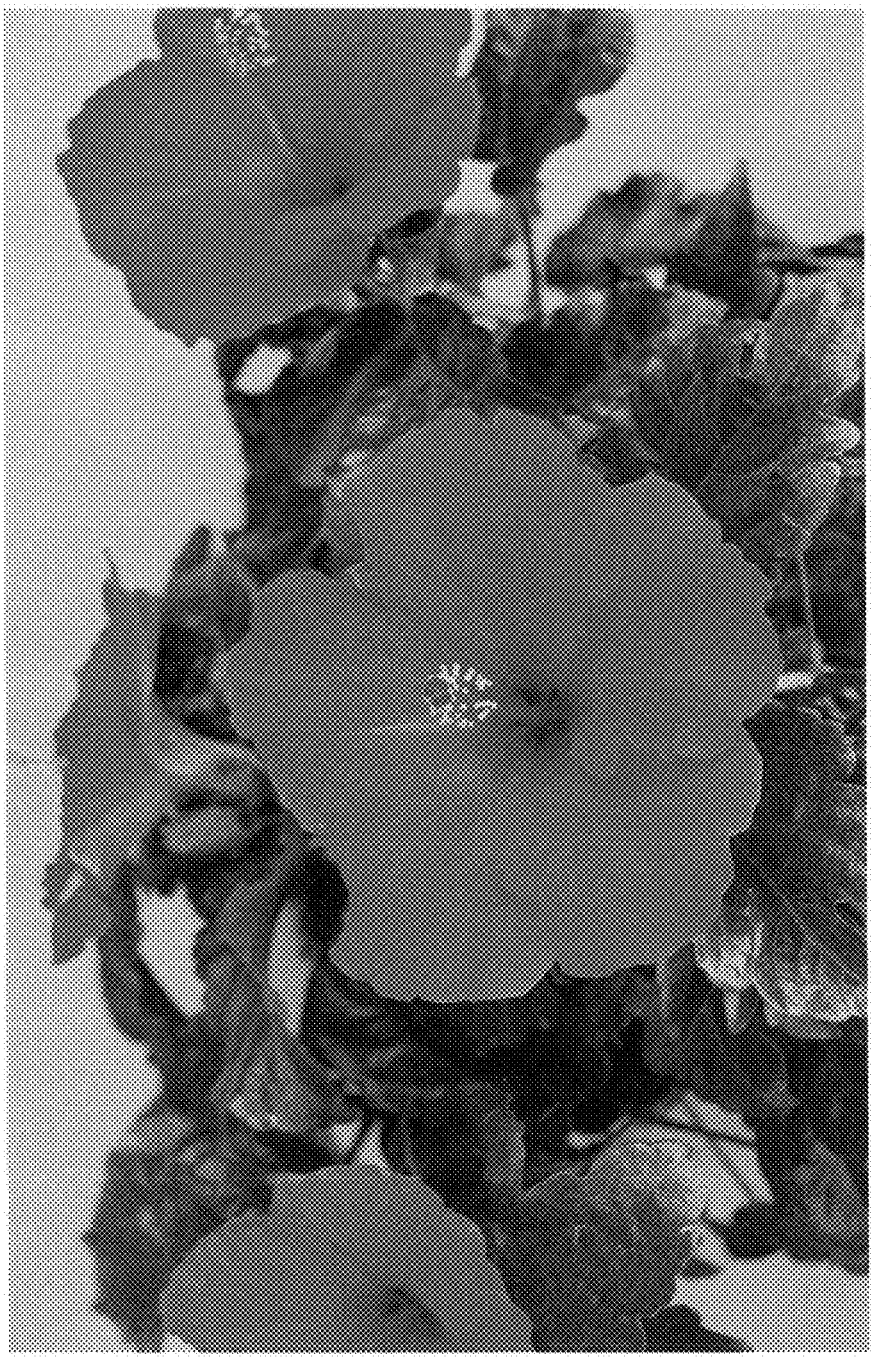

* * * * *